United States Patent
Maiorino et al.

(10) Patent No.: US 9,527,221 B2
(45) Date of Patent: Dec. 27, 2016

(54) METHOD OF FORMING BARBS ON A SUTURE

(71) Applicant: Covidien LP, Mansfield, MA (US)

(72) Inventors: Nicholas Maiorino, Branford, CT (US);
Mark S. Buchter, Ansonia, CT (US);
Matthew D. Cohen, Berlin, CT (US);
Michael Primavera, Orange, CT (US);
Timothy D. Kosa, Hamden, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/254,272

(22) Filed: Apr. 16, 2014

(65) Prior Publication Data
US 2014/0224095 A1 Aug. 14, 2014

Related U.S. Application Data

(63) Continuation of application No. 13/348,006, filed on Jan. 11, 2012, now Pat. No. 8,726,481, which is a (Continued)

(51) Int. Cl.
*B26D 3/08* (2006.01)
*A61B 17/06* (2006.01)
*A61B 17/00* (2006.01)

(52) U.S. Cl.
CPC .......... *B26D 3/08* (2013.01); *A61B 17/06166* (2013.01); *A61B 2017/00526* (2013.01); *A61B 2017/00893* (2013.01); *A61B 2017/06176* (2013.01); *Y10T 29/49* (2015.01); *Y10T 29/49885* (2015.01); *Y10T 83/02* (2015.04); *Y10T 83/0333* (2015.04);
(Continued)

(58) Field of Classification Search
CPC .............. B26D 3/08; A61B 17/06166; A61B 2017/00893; A61B 2017/00526; A61B 2017/06176; Y10T 83/0385; Y10T 83/0333; Y10T 83/02; Y10T 83/0341; Y10T 29/49; Y10T 29/49885; Y10T 29/20; Y10T 29/207; Y10T 29/49801
See application file for complete search history.

(56) References Cited

U.S. PATENT DOCUMENTS 3,482,360 A * 12/1969 Legge ...................... B23Q 5/22
408/130
4,646,595 A 3/1987 Slee
(Continued)

FOREIGN PATENT DOCUMENTS

JP 07266298 10/1995
WO 03017850 A2 3/2003
(Continued)

OTHER PUBLICATIONS

European Search Report for EP 08253030.4-2310 date of completion is Sep. 18, 2009 (3 pages).
(Continued)

*Primary Examiner* — John C Hong

(57) ABSTRACT

A method is provided for forming a barbed medical device which includes the steps of providing a blank workpiece and forming at least one barb on the blank workpiece by applying vibrational energy to a tool and bringing the tool and the blank workpiece into contact with each other at an angle such that the tool cuts into the surface of the blank workpiece. A barbed medical device formed by this method is also provided.

13 Claims, 6 Drawing Sheets

Related U.S. Application Data continuation of application No. 12/178,361, filed on Jul. 23, 2008, now Pat. No. 8,161,618.

(60) Provisional application No. 60/994,173, filed on Sep. 17, 2007.

(52) U.S. Cl.
CPC ......... *Y10T 83/0341* (2015.04); *Y10T 83/0385* (2015.04)

(56) References Cited

U.S. PATENT DOCUMENTS

| | | | |
|---|---|---|---|
| 5,779,025 A * | 7/1998 | Dangelmayr | B21D 43/05 198/621.1 |
| 6,241,747 B1 | 6/2001 | Ruff | |
| 6,270,517 B1 | 8/2001 | Brotz | |
| 6,599,310 B2 | 7/2003 | Leung et al. | |
| 6,848,152 B2 | 2/2005 | Genova et al. | |
| 7,056,331 B2 | 6/2006 | Kaplan et al. | |
| 7,225,512 B2 | 6/2007 | Genova et al. | |
| 7,226,468 B2 | 6/2007 | Ruff | |
| 7,913,365 B2 * | 3/2011 | Genova | A61B 17/06166 164/165 |
| 8,032,996 B2 | 10/2011 | Trull et al. | |
| 8,443,506 B2 | 5/2013 | Maiorino et al. | |
| 8,726,481 B2 | 5/2014 | Maiorino et al. | |
| 2003/0041426 A1 | 3/2003 | Genova et al. | |
| 2003/0149447 A1 | 8/2003 | Morency et al. | |
| 2004/0060409 A1 | 4/2004 | Leung et al. | |
| 2004/0060410 A1 | 4/2004 | Leung et al. | |
| 2004/0088003 A1 | 5/2004 | Leung et al. | |
| 2004/0226427 A1 | 11/2004 | Trull et al. | |
| 2004/0237736 A1 | 12/2004 | Genova et al. | |
| 2005/0234480 A1 | 10/2005 | Nam et al. | |
| 2005/0267531 A1 | 12/2005 | Ruff et al. | |
| 2006/0111734 A1 | 5/2006 | Kaplan et al. | |
| 2006/0111742 A1 | 5/2006 | Kaplan et al. | |
| 2006/0135994 A1 | 6/2006 | Ruff et al. | |
| 2006/0135995 A1 | 6/2006 | Ruff et al. | |
| 2007/0005109 A1 | 1/2007 | Popadiuk et al. | |
| 2007/0065663 A1 | 3/2007 | Trull et al. | |
| 2007/0187861 A1 | 8/2007 | Genova et al. | |
| 2007/0224237 A1 | 9/2007 | Hwang et al. | |
| 2007/0257395 A1 | 11/2007 | Lindh et al. | |
| 2008/0058869 A1 | 3/2008 | Stopek et al. | |
| 2008/0082113 A1 | 4/2008 | Bishop et al. | |
| 2008/0195147 A1 | 8/2008 | Stopek | |
| 2008/0221618 A1 | 9/2008 | Chen et al. | |
| 2008/0281357 A1 | 11/2008 | Sung et al. | |
| 2008/0312688 A1 | 12/2008 | Nawrocki et al. | |
| 2009/0140012 A1 | 6/2009 | Greer, Jr. et al. | |
| 2009/0248066 A1 | 10/2009 | Wilkie | |
| 2009/0287245 A1 | 11/2009 | Ostrovsky et al. | |
| 2010/0084780 A1 | 4/2010 | Lindh, Sr. et al. | |
| 2011/0046669 A1 | 2/2011 | Goraltchouk et al. | |
| 2011/0125188 A1 | 5/2011 | Goraltchouk et al. | |
| 2011/0288583 A1 | 11/2011 | Goraltchouk et al. | |
| 2012/0046675 A1 | 2/2012 | Bishop et al. | |

FOREIGN PATENT DOCUMENTS

| | | |
|---|---|---|
| WO | 2007131019 A2 | 11/2007 |
| WO | 2008042992 A2 | 4/2008 |
| WO | 2008112417 A2 | 9/2008 |
| WO | 2008117328 A2 | 10/2008 |
| WO | 2008141034 A1 | 11/2008 |
| WO | 2008157142 A2 | 12/2008 |
| WO | 2009105663 A2 | 8/2009 |
| WO | 2009129251 A2 | 10/2009 |
| WO | 2009132284 A2 | 10/2009 |
| WO | 2009140012 A1 | 11/2009 |

OTHER PUBLICATIONS

European Search Report for EP 10 25 0848 dated Aug. 12, 2010 (completed Jul. 26, 2010) (3 pages).
European Search Report for EP 12164986.7-2310 date of completion is Jun. 22, 2012 (6 pages).
European Search Report EP 12 16 5912 dated Jul. 18, 2012.
European Search Report EP 12 16 9376 dated Sep. 12, 2012.
European Search Report EP 12 16 9370 dated Sep. 12, 2012.
Canadian Office Action from Application No. 2,639,445 dated Jun. 25, 2015.
Chinese Office Action, and English language translation, from Application No. 201310187814.6 dated Jul. 3, 2015.
Chinese Office Action, and English Translation, from Chinese Application No. 201310187814.6 dated Dec. 28, 2015.
EP Communication from Appl. No. 12164986.7 dated Jun. 22, 2016.

* cited by examiner

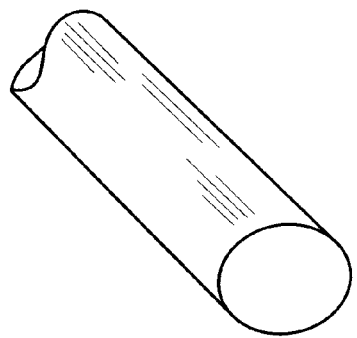
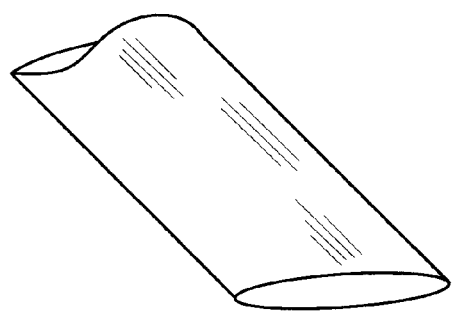
FIG. 2A   FIG. 2B
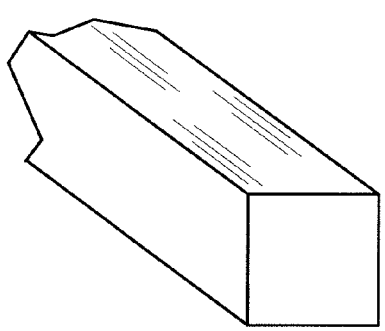
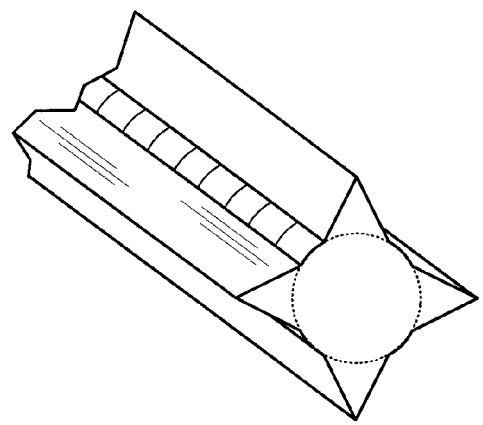
FIG. 2C   FIG. 2D

METHOD OF FORMING BARBS ON A SUTURE

CROSS-REFERENCE TO RELATED APPLICATIONS

This application is a continuation of U.S. patent application Ser. No. 13/348,006 filed Jan. 11, 2012, now U.S. Pat. No. 8,726,481, which is a continuation of U.S. patent application Ser. No. 12/178,361 filed Jul. 23, 2008, now U.S. Pat. No. 8,161,618, which claims benefit of U.S. Provisional Application No. 60/994,173 filed Sep. 17, 2007, and the disclosures of each of the above-identified applications are hereby incorporated by reference in their entirety.

TECHNICAL FIELD

The present disclosure relates to a method of forming barbs on medical devices, namely forming barbs on sutures using vibrational energy. More particularly, the present disclosure relates to a method of forming barbs on sutures using ultrasonic energy.

BACKGROUND OF RELATED ART

Barbed sutures are generally made of the same materials as conventional sutures and offer several advantages for closing wounds compared with conventional sutures. A barbed suture includes an elongated body that has one or more spaced barbs, that project from the surface of the suture body along the body length. The barbs are arranged to allow passage of the barbed suture in one direction through tissue but resist movement of the barbed suture in the opposite direction. Thus, one advantage of barbed sutures has been the provision of a non-slip attribute.

Barbed sutures are known for use in cosmetic, laparoscopic and endoscopic procedures. The number of barbs called for on a particular suture may be influenced by the size of the wound and the strength required to hold the wound closed. Like a conventional suture, a barbed suture may be inserted into tissue using a surgical needle.

In some circumstances, a random configuration of barbs on the exterior surface of the suture is preferred to achieve optimal wound closure holding for the particular wound. However, in other circumstances, where the wound or tissue repair needed is relatively small, a reduced number of barbs may be desired. In other circumstances, a two way barbed suture is desirable where the barbs permit passing of the suture in one direction over a portion of the suture and barbs permitting passing of the suture in a second direction over another portion of the suture to perform a tight closing stitch.

Various methods of forming barbs on sutures have been proposed such as mechanical cutting, laser cutting, injection molding, stamping, extrusion and the like. However, such methods may be difficult or costly to achieve the desired result with respect to getting the arrangement of barbs in a configuration needed for the appropriate procedure and for doing so in an efficient cost effective manner.

Conventional cutting methods of forming barbs have significant drawbacks in their ability to maintain sharpness, move rapidly, part cost and have slow manufacturing cycle time.

Accordingly, there is a continuing need for methods of forming barbs on a suture that are less difficult, more effective and economical. There is also a continuing need for methods which are able to vary the size of the barbs, the location and the depth, as well as a need for determining the amount of the barbs needed on a suture for the type of tissue to be repaired.

SUMMARY

A method is provided for forming a barbed medical device which includes the steps of providing a blank workpiece and forming at least one barb on the blank workpiece by applying vibrational energy to a tool and bringing the tool and the blank workpiece into contact at an angle such that the tool cuts into the surface of the blank workpiece.

The tool provided may be a knife or rotary blade formed of geometrical shapes such as a rectangle, a square, a circle, flat, a star, an octagon, a triangle, a spade, an arrow, a key and an ellipse.

In exemplary embodiments, the vibrational energy may be ultrasonic energy and is applied to the blank workpiece by providing a converter which communicates ultrasonic energy to a horn operatively coupled to the converter.

A barbed medical device formed by the method in accordance with the present disclosure is provided.

A method is provided for forming a barbed suture which includes the steps of providing a suture and forming at least one barb on the suture by applying vibrational energy to a tool and bringing the tool and the suture into contact at an angle such that the tool cuts into the surface of the suture. A method of closing a wound with the barbed suture formed by the method in accordance with the present disclosure is also provided.

BRIEF DESCRIPTION OF THE DRAWINGS

Various embodiments of the present disclosure will be described herein below with reference to the figures wherein:

FIGS. 2A-G are partial perspective views of alternative embodiments of the geometry of blank workpieces in accordance with the present disclosure;

DETAILED DESCRIPTION

In general, disclosed herein is a method of forming a barbed medical device by providing a blank workpiece and forming at least one barb on the blank workpiece by vibrating a tool, such as a knife, with energy and bringing the knife and the workpiece in contact with one another to cut into the surface of the workpiece a predetermined depth, angle, and length thereby forming a barb. The present disclosure illustrates and describes the method by way of the illustrative example of applying ultrasonic energy to the tool, e.g., knife. However, it is contemplated and within the scope of the present disclosure that the tool or knife may be vibrated by other forms of energy.

Figure 1:
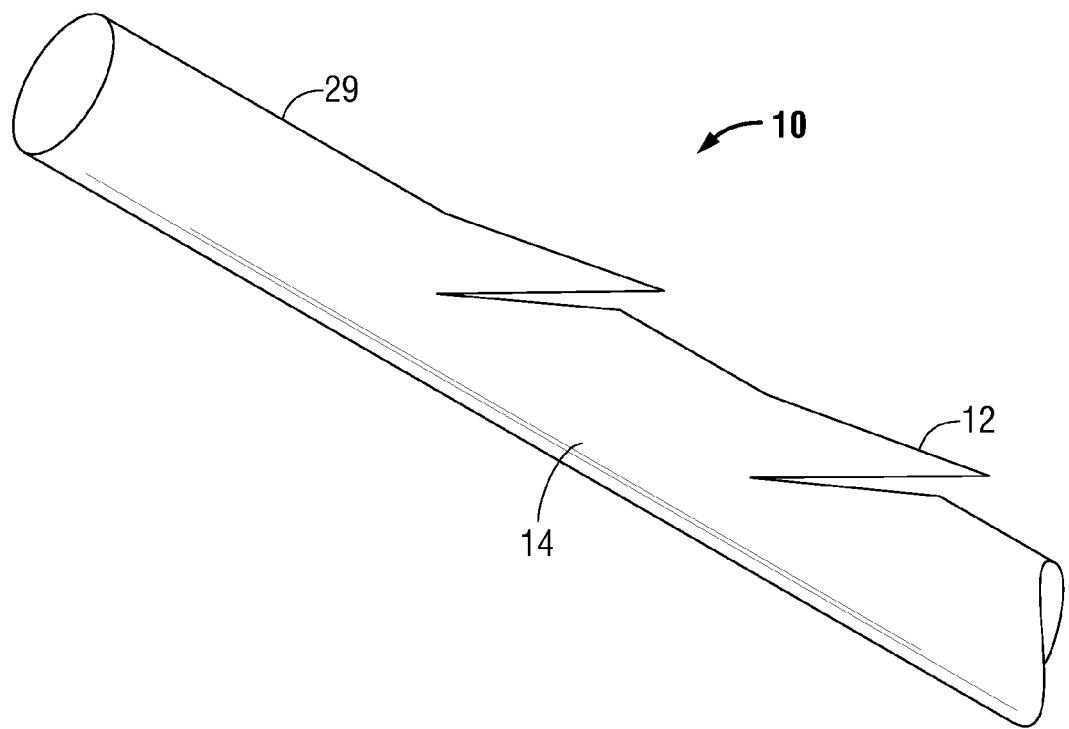
FIG. 1 is a perspective view of a barbed suture formed in accordance with the present disclosure.

Referring now in detail to the drawings in which like reference numerals are applied to like elements in the various views, FIG. 1 illustrates a medical device 10 having an elongated body 14 and a plurality of barbs 12 formed thereon.

The medical device 10 has a proximal and distal end. As shown in the exemplary embodiment of FIG. 1, the barbs 12 may be formed projecting from the blank workpiece 29 towards at least one end. In other embodiments, multiple barbs may be formed such that a portion of the barbs project toward one end and the remaining portion of the barbs project toward the other end so as to form a two way medical device. The barbs 12 as formed have an angle of less than 90 degrees between the barbs 12 and the wound closure elongated body 14.

The blank workpiece 29 in accordance with the present disclosure may be formed of the type selected from the group consisting of monofilament sutures, braided sutures, multifilament sutures, surgical fibers, anchors, slit sheets, ribbons, tape, mesh, stent, scaffolds, pledgets, vascular graft and ribbons.

Figure 2E:
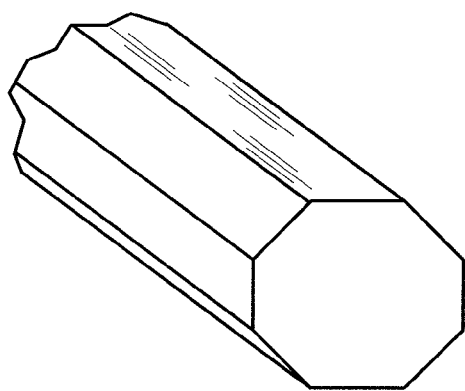
Figure 2F:
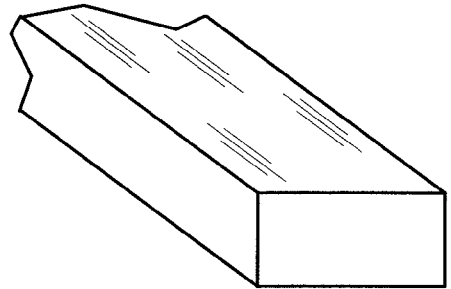
Figure 2G:
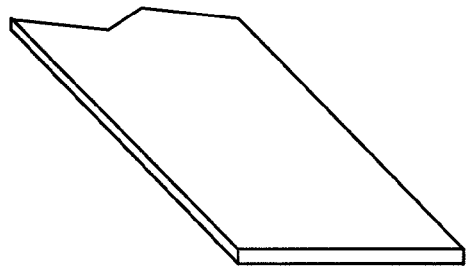

The blank workpiece from which the exemplary medical device 10 of FIG. 1 is formed is circular in cross-sectional geometry. However, the cross-sectional geometry of the blank workpiece may be of any suitable shape. For example, FIGS. 2A-2G illustrate cross-sectional views of alternative embodiments of the various cross-sectional geometries of the blank workpiece in accordance with the present disclosure, namely, round (FIG. 2A), elliptical (FIG. 2B), square (FIG. 2C), star shaped (FIG. 2D), octagonal (FIG. 2E), rectangular (FIG. 2F), and flat (FIG. 2G).

Figure 3:
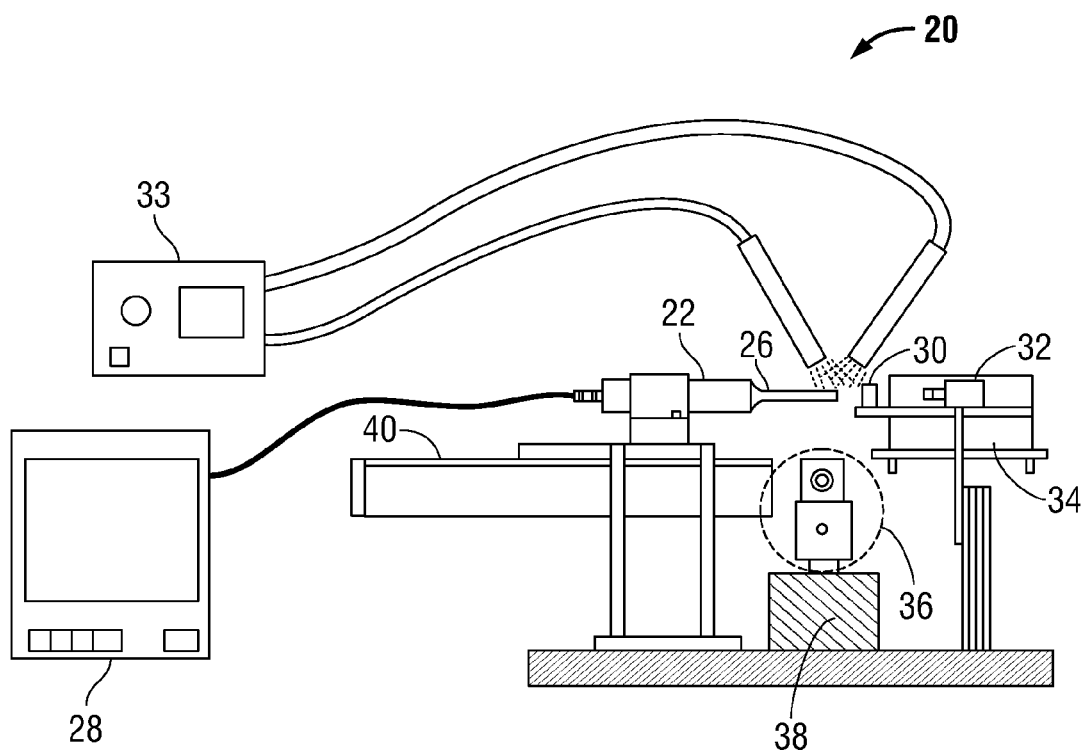
FIG. 3 is a schematic view of one embodiment of an apparatus and method of forming barbs on a blank workpiece in accordance with the present disclosure.

FIG. 3 illustrates an embodiment of an apparatus and method of forming barbs in accordance with the present disclosure. In the illustrative embodiment of FIG. 3, the ultrasonic energy is generated by an apparatus 20 that includes a converter 22 which transmits ultrasonic energy to a horn 26 that is operatively coupled to the converter 22. The converter 22 converts electrical energy to mechanical energy which causes displacement of the tool at a predetermined ultrasonic frequency powered by an ultrasonic generator or booster 28. Booster 28 may be manipulated to either increase or decrease the ultrasonic frequency which may be transmitted to the tool. The ultrasonic frequency may range from about 1 kHz to about 100 kHz. In other embodiments, the ultrasonic frequency may range from about 10 kHz to about 90 kHz. In still further embodiments, the ultrasonic frequency may range from about 15 kHz to about 50 kHz. The ultrasonic signal amplitude may range from about 1μ to about 125μ. In other embodiments, the signal amplitude may range from about 15μ to about 60μ.

The depth and the angle of the barbs relative to the elongated body of the medical device are variable based on the signal amplitude of ultrasonic energy applied to the cutting element. For example, as the ultrasonic amplitude is increased, the ratio of the cut and the angle of the barbs are decreased. As the ultrasonic amplitude is increased, the depth of the cut is increased.

With continued reference to FIG. 3, the apparatus 20 optionally includes a gripper such as anvil 30 for supporting a blank workpiece 29. The gripper 30 supports the blank workpiece 29 (FIG. 1) at a fixed position. The horn 26 is configured and dimensioned to accept a tool, e.g., a knife blade (FIGS. 4A-4M), a rotary blade (not shown), or the like, for forming the barbs on the blank workpiece. Apparatus 20 optionally includes camera 32 for recording the method of forming barbs and a light source 33 for optimizing the view of camera 32. The motorized slide 34 moves in an X, Y, and Z plane to allow the blank workpiece to pass in front of the converter 22 to form barbs thereon. Apparatus 20 also includes rotational motor 36 which rotates the blank workpiece in a circular direction. Advance slide 38 moves the blank workpiece after every cut a predetermined increment for the appropriate barb spacing.

In embodiments, the blank workpiece is moved in a linear or perpendicular motion relative to the horn. The amount of time the blade is in contact with the blank workpiece ranges, in embodiments, from about 1 millisecond to about 5 seconds. In other embodiments, the amount of time the blade is in contact with the blank workpiece ranges from about 1 second to about 3 seconds. In still further embodiments, the amount of time the blade is in contact with the blank workpiece is about 2 seconds.

Figure 4A:
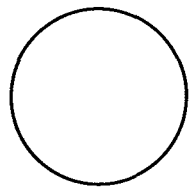
FIGS. 4A-M are transverse cross-sectional views of alternative embodiments of the geometry of the knife blade shape in accordance with the present disclosure.
Figure 4B:
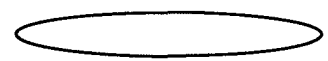
Figure 4C:
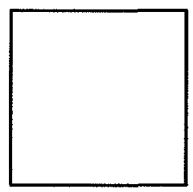
Figure 4D:
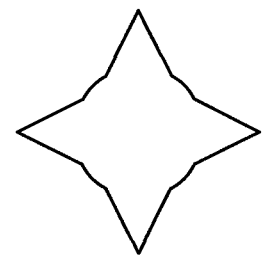
Figure 4E:
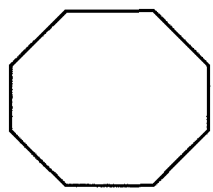
Figure 4F:
Figure 4G:
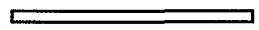
Figure 4H:
Figure 4I:
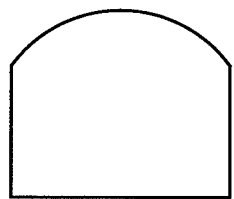
Figure 4J:
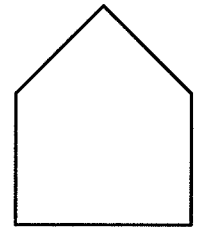
Figure 4K:
Figure 4L:
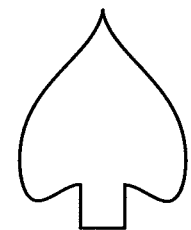
Figure 4M:
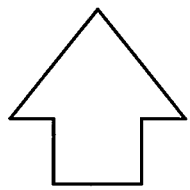

FIGS. 4A through 4M illustrate alternative embodiments of various geometries of an ultrasonic knife blade in accordance with the present disclosure, namely, a circle (FIG. 4A), an ellipse (FIG. 4B), a square (FIG. 4C), a star (FIG. 4D), an octagon (FIG. 4E), a rectangle (FIG. 4F), a flat shape (FIG. 4G), a triangle (FIG. 4J), a key (FIG. 4K), a spade (FIG. 4L), an arrow (FIG. 4M), and combinations thereof. The curvature of the rotary blade may also include a substantially concave shape (FIG. 4H) and a substantially convex shape (FIG. 4I).

In practice, the blank workpiece passes in front of the converter 22 which includes the horn 26 and the anvil 30, then using ultrasonic energy at various frequencies and signal amplitudes cut the material to a predetermined geometry. In embodiments, the blank workpiece passes in front of the converter via motorized slide 34 which is configured and dimensioned to hold gripper 30 and camera 32 thereon. In certain embodiments, the blank workpiece passes in front of converter 22, via a mechanical feeding mechanism with the blank workpiece held tightly around two spools on each side of the apparatus (not shown). In other embodiments, the blank workpiece passes in front of converter 22 via human manipulation of the blank workpiece.

The apparatus includes a converter 22 coupled to a horn 26 which operatively moves along a straight line X-Y plane via ultrasonic vibrational energy. The horn 26 includes a blade which contacts a surface of the blank workpiece at an angle so as to form at least one barb on the blank workpiece. The blade is appropriately positioned to contact the blank workpiece via knife positioning slide 40. After each barb is formed, the blank workpiece is moved in a linear motion on a X-Y plane via motorized slide 34 a predetermined length to allow another barb to be formed thereon. In embodiments, the blank workpiece is moved in a X-Z plane via motorized slide 34 a predetermined length to form a barb thereon. In further embodiments, the blank workpiece is moved in a Y-Z plane via motorized slide 34 a predetermined length to form a barb thereon. In alternative embodiments, the blank workpiece is moved in a circular manner via rotational motor 36 to form a barb at a predetermined position. In embodiments, the blank workpiece is moved in both a rotational and x-z plane rotation.

In practice, the barbs 12 are formed as either the knife blade 24 or rotary blade (not shown) contacts the outer surface of the blank workpiece 29. The blade may be urged into contact with the surface of the blank workpiece 29, for example, by a reciprocating actuator in a straight line X-Y plane. It is contemplated, however, that in alternative embodiments, the blade may be held fixed and the workpiece 29 may be urged toward the blade. The blade makes contact with the surface of the blank workpiece 29 at an angle relative thereto such that the combined action of the movement of the blade into contact with the workpiece surface and the ultrasonic vibration of the knife forms the desired barb. Advance slide 38 then moves the blank workpiece after every cut a predetermined increment for the desired spacing of the barbs.

Ultrasonic energy may transfer heat to the blank workpiece 29 as it is forming the barbs 12 thereon. Depending on the strength of the amplitude, the ultrasonic frequency may cause melting of blank workpiece 29 if the blades are left to penetrate blank workpiece 29 throughout the full wave cycle. To prevent this from occurring, in some embodiments, the application of ultrasonic energy is discontinued at some point prior to withdrawal of the blades from contact of the blank workpiece 29. In other embodiments, this method may be used to vary the angle and the depth of the cut as indicated above with respect to the increase or decrease of the amplitude.

In some embodiments, barbs may be formed by making acute angular cuts directly into the blank workpiece body, with cut portions pushed outwardly and separated from the body of the blank workpiece. The depth of the barbs thus formed in the blank workpiece body may depend on the diameter of the material and the depth of the cut.

In some embodiments, a suitable device for cutting a plurality of axially spaced barbs on the exterior of a filament may use an gripper as a cutting bed, a cutting bed vise, a cutting template, and an converter and horn as the blade assembly to perform the cutting. In operation, the cutting device has the ability to produce a plurality of axially spaced barbs in the same or random configuration and at different angles in relation to each other.

In other embodiments, the barbs may be aligned on a first portion of a length of the blank workpiece body to allow movement of a first end of the medical device through tissue in one direction, while barbs on a second portion of the length of the blank workpiece body may be aligned to allow movement of the second end of the medical device in an opposite direction.

The barbs may be arranged in any suitable pattern, for example, helical, linear, or randomly spaced. The pattern may be symmetrical or asymmetrical. The number, configuration, spacing and surface area of the barbs may vary depending upon the tissue in which the medical device is used, as well as the composition and geometry of the material utilized to form the medical device. Additionally, the proportions of the barbs may remain relatively constant while the overall length of the barbs and the spacing of the barbs may be determined by the tissue being connected. For example, if the medical device is to be used to connect the edges of a wound in skin or tendon, the barbs may be made relatively short and more rigid to facilitate entry into this rather firm tissue. Alternatively, if the medical device is intended for use in fatty tissue, which is relatively soft, the barbs may be made longer and spaced further apart to increase the ability of the suture to grip the soft tissue.

The surface area of the barbs may also vary. For example, fuller-tipped barbs may be made of varying sizes designed for specific surgical applications. For joining fat and relatively soft tissues, larger barbs may be desired, whereas smaller barbs may be more suitable for collagen-dense tissues. In some embodiments, a combination of large and small barbs within the same structure may be beneficial, for example when a suture is used in tissue repair with differing layer structures. Use of the combination of large and small barbs with the same suture wherein barb sizes are customized for each tissue layer will ensure maximum anchoring properties. In particular embodiments, a single directional suture may have both large and small barbs; in other embodiments a bi-directional suture may have both large and small barbs. The barbs formed may include geometrical shapes such as round, triangular, square, oblique, elliptical, octagonal, rectangular, and flat In some embodiments, barbs may be formed on the outer surface of anchors which allow movement of the anchor portion through bone in one direction but resist the withdrawal of the anchor portion after the anchor portion has been implanted in the bone.

Blank workpieces 29 in accordance with the present disclosure may be formed of degradable materials, non-degradable materials, and combinations thereof. More particularly, the blank workpiece may be formed of a degradable material selected from the group consisting of polyesters, polyorthoesters, polymer drugs, polyhydroxybutyrates, lactones, proteins, cat gut, collagens, carbonates, homopolymers thereof, copolymers thereof, and combinations thereof. In other embodiments, suitable degradable materials which may be utilized to form the medical device include natural collagenous materials or synthetic resins including those derived from alkylene carbonates such as trimethylene carbonate, tetramethylene carbonate, and the like, caprolactone, dioxanone, glycolic acid, lactic acid, glycolide, lactide, homopolymers thereof, copolymers thereof, and combinations thereof. In some embodiments, glycolide and lactide based polyesters, especially copolymers of glycolide and lactide, may be utilized to form the blank workpiece of the present disclosure.

Barbed medical devices fabricated from a degradable material in accordance with the present disclosure maintain their structural integrity after implantation for a predetermined period of time, depending on the characteristics of the particular copolymer used. Such characteristics include, for example, the components of the copolymer, including both the monomers utilized to form the copolymer and any additives thereto, as well as the processing conditions (e.g., rate of copolymerization reaction, temperature for reaction, pressure, etc.), and any further treatment of the resulting copolymers, i.e., coating, sterilization, etc.

Barbed sutures of the present disclosure typically maintain their structural integrity. For example, the Maxon™ suture, commercially available from U.S. Surgical, a division of Tyco Healthcare, typically maintains 80% of initial tensile strength at 1 week, 75% at 2 weeks, 65% at 3 weeks, 50% at 4 weeks and 25% at 6 weeks post implant. Another example includes Caprosyn™, commercially available from U.S. Surgical, a division of Tyco Healthcare, which provides strong secure wound approximation for 10 days and maintains structural integrity even after multiple passes.

The formation of barbs on a suture body may be utilized to change the degradation time of a suture in accordance with the present disclosure as described in U.S. patent application Ser. No. 11/556,002 filed on Nov. 2, 2006 entitled "Long Term Bioabsorbable Barbed Sutures", the entire contents of which are incorporated by reference herein.

For non-degradable barbed medical devices constructed in accordance with the present disclosure, suitable non-degradable materials which may be utilized to form the medical device include polyolefins, such as polyethylene, polypropylene, copolymers of polyethylene and polypropylene, and blends of polyethylene and polypropylene; polyamides (such as nylon); polyamines, polyimines, polyesters such as polyethylene terephthalate; polytetrafluoroethylene; polyether-esters such as polybutester; polytetramethylene ether glycol; 1,4-butanediol; polyurethanes; and combinations thereof. In other embodiments, non-degradable materials may include silk, collagen, cotton, linen, carbon fibers, and the like. The polypropylene may be isotactic polypropylene or a mixture of isotactic and syndiotactic or atactic polypropylene.

The filaments and fibers used for forming the blank workpiece of the present disclosure may be formed using any technique within the purview of those skilled in the art, such as, for example, extrusion, molding and/or solvent casting.

In some embodiments, the suture of the present disclosure may include a yarn made of more than one filament, which may contain multiple filaments of the same or different materials. Where the sutures are made of multiple filaments, the suture may be made using any known technique such as, for example, braiding, weaving or knitting. The filaments may also be combined to produce a non-woven suture. The filaments themselves may be drawn, oriented, crinkled, twisted, commingled or air entangled to form yarns as part of the suture forming process. In one embodiment, a multifilament suture of the present disclosure may be produced by braiding. The braiding may be done by any method within the purview of those skilled in the art.

Once the medical device is barbed, it may be sterilized by any means within the purview of those skilled in the art.

Medical devices in accordance with the present disclosure may be coated or impregnated with one or more medico-surgically useful substances which accelerate or beneficially modify the healing process when the medical device is applied to a wound or surgical site. In certain embodiments, the coating may be formed from degradable polymers selected from the group consisting of lactones, carbonates, polyorthoesters, hydroxyalkoanates, hydroxybutyrates, bioactive agents, polyanhydrides, silicone, calcium stearoyl lactylates, vinyl polymers, high molecular weight waxes and oils, natural polymers, proteins, polysaccharides, suspendable particulates, dispersible particulates, microspheres, nanospheres, rods, homopolymers thereof, copolymers thereof, and combinations thereof.

Suitable bioactive agents include, for example, biocidal agents, antimicrobial agents, antibiotics, anti-proliferatives, medicants, growth factors, anti-clotting agents, clotting agents, analgesics, anesthetics, anti-inflammatory agents, wound repair agents and the like, chemotherapeutics, biologics, protein therapeutics, monoclonal or polyclonal antibodies, DNA, RNA, peptides, polysaccharides, lectins, lipids, probiotics, diagnostic agents, angiogenics, anti-angiogenic drugs, polymeric drugs, and combinations thereof.

Bioactive agents include substances which are beneficial and tend to promote the healing process. For example, a suture can be provided with a bioactive agent that will be deposited at the sutured site. The bioactive agent can be chosen for its antimicrobial properties, capability for promoting wound repair and/or tissue growth, or for specific indications such as thrombosis. In embodiments, combinations of such agents may be applied to the medical device of the present disclosure after formation of the barbs.

The term "antimicrobial agent" as used herein includes an agent which by itself or through assisting the immune system, helps the body destroy or resist microorganisms which may be pathogenic. An antimicrobial agent includes antibiotics, antiseptics, quorum sensing blockers, antifungals, anti-virals, surfactants, metal ions, antimicrobial proteins and peptides, antimicrobial polysaccharides, disinfectants and combinations thereof. Antimicrobial agents which are slowly released into the tissue can be applied in this manner to aid in combating clinical and sub-clinical infections in a surgical or trauma wound site. In embodiments, suitable antimicrobial agents may be soluble in one or more solvents.

In embodiments, the following anti-microbial agents may be used alone or in combination with other bioactive agents described herein: an anthracycline, doxorubicin, mitoxantrone, a fluoropyrimidine, 5-fluorouracil (5-FU), a folic acid antagonist, methotrexate, mitoxantrone, quorum sensing blocker, brominated or halogenated furanones, a podophylotoxin, etoposide, camptothecin, a hydroxyurea, a platinum complex, cisplatin, doxycycline, metronidazole, trimethoprim-sulfamethoxazole, rifamycins like rifampin, a fourth generation penicillin (e.g., a ureidopenicillin a carboxypenicillin, meziocillin, piperacillin, carbenicillin, and ticarcillin, and an analogue or derivative thereof), a first generation cephalosporin (e.g., cephazolin sodium, cephalexin, cefazolin, cephapirin, and cephalothin), a carboxypenicillin (e.g., ticarcillin), a second generation cephalosporin (e.g., cefuroxime, cefotetan, and cefoxitin), a third generation cephalosporin (e.g., naxcel, cefdinir, cefoperazone, ceftazidime, ceftriaxone, and cefotaxime), polyvinyl pyrrolidone (PVP), a fourth generation cephalosporin (e.g., cefepime), a monobactam (e.g., aztreonam), a carbapenem (e.g., imipenem, ertapenem and meropenem), an aminoglycoside (e.g., streptomycin, gentamicin, tobramycin, and amikacin), an MSL group member (e.g., a macrolide, a long acting macrolide, a lincosamide, a streptogramin, Erythromycin, Azithromycin, Clindamycin, Syneroid, clarithromycin, and kanamycin sulfate), tetracyclines like minocycline, fusidic acid, trimethoprim, metronidazole; a quinolone (e.g., ciprofloxacin, ofloxacin, gatifloxacin, moxifloxacin, levofloxacin, and trovafloxacin), a DNA synthesis inhibitor (e.g., metronidazole), a sulfonamide (e.g. sulfamethoxazole, trimethoprim, including cefixime, spectinomycin, tetracycline, nitrofurantoin, polymyxin B, and neomycin sulfate), beta-lactam inhibitors like sulbactam, chloramphenicol, glycopeptides like vancomycin, mupirocin, polyenes like amphotericin B, azoles like fluconazole, and other known antimicrobial agent known in the art.

Examples of chemotherapeutics which may be utilized include one or more of the following: doxorubicin (Dox), paclitaxel (PTX), or camptothecin (CPT), polyglutamate-PTX (CT-2103 or Xyotax), N-(2-hydroxypropyl)methacrylamide (HPMA) copolymer, anthracycline, mitoxantrone, letrozole, anastrozole, epidermal growth factor receptor inhibitors, tyrosine kinase inhibitors, modulators of apoptosis, anthracycline antibiotics such as daunorubicin and doxorubicin, alkylating agents such as cyclophosphamide and melphalan, antimetabolites such as methotrexate and 5-fluorouracil, poly(ethylene glycol) (PEG), poly(glutamic acid) (PGA), polysaccharides, monoclonal antibody and polymer-drug conjugates thereof, copolymers thereof and combinations thereof.

The clotting agents include one or more of the following: a fibrosing agent that promotes cell regeneration, a fibrosing agent that promotes angiogenesis, a fibrosing agent that promotes fibroblast migration, a fibrosing agent that promotes fibroblast proliferation, a fibrosing agent that promotes deposition of extracellular matrix, a fibrosing agent that promotes tissue remodeling, a fibrosing agent that is a diverticular wall irritant, silk (such as silkworm silk, spider silk, recombinant silk, raw silk, hydrolyzed silk, acid-treated silk, and acylated silk), talc, chitosan, bleomycin or an analogue or derivative thereof, connective tissue growth factor (CTGF), metallic beryllium or an oxide thereof, copper, saracin, silica, crystalline silicates, quartz dust, talcum powder, ethanol, a component of extracellular matrix, oxidized cellulose, polysaccharides, collagen, fibrin, fibrinogen, poly(ethylene terephthalate), poly(ethylene-co-vinylacetate), N-carboxybutylchitosan, an RGD protein, a polymer of vinyl chloride, cyanoacrylate, crosslinked poly (ethylene glycol)-methylated collagen, an inflammatory cytokine, TGFβ, PDGF, VEGF, TNFa, NGF, GM-CSF, IGF-a, IL-1, IL-8, IL-6, a growth hormone, a bone morphogenic protein, a cell proliferative agent, dexamethasone, isotretinoin, 17-β-estradiol, estradiol, diethylstibesterol, cyclosporine a, all-trans retinoic acid or an analogue or derivative thereof, wool (including animal wool, wood wool, and mineral wool), cotton, bFGF, polyurethane, polytetrafluoroethylene, activin, angiopoietin, insulin-like growth factor (IGF), hepatocyte growth factor (HGF), a colony-stimulating factor (CSF), erythropoietin, an interferon, endothelin-1, angiotensin II, bromocriptine, methylsergide, fibrosin, fibrin, an adhesive glycoprotein, proteoglycan, hyaluronan, secreted protein acidic and rich in cysteine (SPaRC), a thrombospondin, tenacin, a cell adhesion molecule, dextran based particles, an inhibitor of matrix metalloproteinase, magainin, tissue or kidney plasminogen activator, a tissue inhibitor of matrix metalloproteinase, carbon tetrachloride, thioacetamide, superoxide dismutase to scavenge tissue-damaging free radicals, tumor necrosis factor for cancer therapy, colony stimulating factor, interferon, interleukin-2 or other lymphokines to enhance the immune system, platelet rich plasma, thrombin, peptides such as self assembly peptide systems, amino acids such as radA based amino acids, hydrogels such as super absorbing hydrogel materials, combinations thereof, and so forth.

A wide variety of anti-angiogenic factors may be readily utilized within the context of the present disclosure. Representative examples include Anti-Invasive Factor; retinoic acid and derivatives thereof; paclitaxel a highly derivatized diterpenoid; Suramin; Tissue Inhibitor of Metalloproteinase-1; Tissue Inhibitor of Metalloproteinase-2; Plasminogen Activator Inhibitor-1; Plasminogen Activator Inhibitor-2; various forms of the lighter "d group" transition metals such as, for example, vanadium, molybdenum, tungsten, titanium, niobium, and tantalum species and complexes thereof; Platelet Factor 4; Protamine Sulphate (Clupeine); Sulphated Chitin Derivatives (prepared from queen crab shells); Sulphated Polysaccharide Peptidoglycan Complex (SP-PG) (the function of this compound may be enhanced by the presence of steroids such as estrogen, and tamoxifen citrate); Staurosporine; Modulators of Matrix Metabolism, including for example, proline analogs {[(L-azetidine-2-carboxylic acid (LACA), cishydroxyproline, d,L-3,4-dehydroproline, Thiaproline, α,α-dipyridyl, β-aminopropionitrile fumarate; MDL 27032 (4-propyl-5-(4-pyridinyl)-2(3H)-oxazolone; Methotrexate; Mitoxantrone; Heparin; Interferons; 2 Macroglobulin-serum; ChIMP-3; Chymostatin; β-Cyclodextrin Tetradecasulfate; Eponemycin; Camptothecin; Fumagillin Gold Sodium Thiomalate ("GST"); D-Penicillamine ("CDPT"); β-1-anticollagenase-serum; α2-antiplasmin; Bisantrene; Lobenzarit disodium (N-(2)-carboxyphenyl-4-chloroanthronilic acid disodium or "CCA"; Thalidomide; Angostatic steroid; AGM-1470; carboxynaminolmidazole; metalloproteinase inhibitors such as BB94, analogues and derivatives thereof, and combinations thereof.

A wide variety of polymeric drugs may be readily utilized within the context of the present disclosure. Representative examples include steroidal anti-inflammatory agents, non-steroidal anti-inflammatory agents, and combinations thereof. Examples of the non-steroidal anti-inflammatory agent which may be used with the present disclosure are aspirin, indomethacin, ibuprofen, phenylbutazone, diflusinal, and combinations thereof.

Examples of the steroidal anti-inflammatory agent which may be used are glucocorticoids such as cortisone and hydrocortisone, betamethasone, dexamethasone, fluprednisolone, prednisone, methylprednisolone, prednisolone, triamcinolone, paramethasone, and combinations thereof.

Although the above bioactive agents have been provided for the purposes of illustration, it should be understood that the present disclosure is not so limited. In particular, although certain bioactive agents are specifically referred to above, the present disclosure should be understood to include analogues, derivatives and conjugates of such agents.

Medical devices in accordance with this disclosure may also include, for example, biologically acceptable plasticizers, antioxidants and colorants, which may be impregnated into the filament(s) utilized to form a suture of the present disclosure or included in a coating thereon.

Bioactive agents may be applied onto a barbed medical device of the present disclosure utilizing any method within the purview of one skilled in the art including, for example, dipping, spraying, vapor deposition, brushing, solvent evaporation, compounding and the like. In embodiments, a bioactive agent may be deposited within the barb angles, that is, the angle formed between the barb and the blank workpiece surface in accordance with the present disclosure as described in U.S. patent application Ser. No. 11/899,852 filed on Sep. 6, 2007 entitled "Bioactive Substance in a Barbed Sutures", the entire contents of which are incorporated by reference herein.

Placement of a bioactive agent in the angle formed between the barbs and blank workpiece surface places the bioactive agent at precisely defined locations within a tissue wound closure, which thereby provides a unique controlled and sustained release dosage form.

Blank workpieces of the present disclosure may be dyed in order to increase the visibility of the workpiece in the surgical field. Any dye suitable for incorporation in medical devices may be used. Such dyes include, but are not limited to, carbon black, bone black, D&C Green No. 6, and D&C Violet No. 2. Filaments in accordance with the present disclosure may be dyed by adding dye in an amount up to about a few percent; in other embodiments, they may be dyed by adding dye in an amount of about 0.2%; in still further embodiments, the dye may be added in an amount from about 0.06% to about 0.08%.

The filaments and sutures of the present disclosure may additionally comprise a needle at one end. In order to facilitate needle attachment to a suture of the present disclosure, conventional tipping agents may be applied to the braid. Two tipped ends of the suture may be desirable for attaching a needle to each end of the suture to provide a so-called double armed suture. The needle attachment may be made by any conventional method such as crimping, swaging, and the like.

In some cases, a tubular insertion device (not shown) may be utilized to introduce a barbed medical device in accordance with the present disclosure into tissue. Such a tubular insertion device may have a tubular body in which the barbed medical device of the present disclosure is disposed, as well as a distal end and a proximal end. In some embodiments, the pointed end of a barbed suture of the present disclosure may be pushed with the distal end of the tubular insertion device through skin, tissue, and the like at an insertion point. The pointed end of the suture and the distal end of the tubular insertion device are pushed through the tissue until reaching an endpoint. The proximal end of the tubular insertion device is then gripped and pulled to remove the insertion device, leaving the barbed suture in place.

Barbed sutures and placement methods suitable for use according to the present disclosure are well known in the art. For example, in embodiments, medical devices of the present disclosure may be utilized to provide lift to tissue, which may be desirable in certain cosmetic applications. In some embodiments, a procedure for closing tissue utilizing barbed sutures includes inserting a first end of the suture, optionally attached to a needle, at an insertion point on the surface of a person's body. The first end of the suture may be pushed through soft tissue until the first end extends out of the soft tissue at an exit point. The first end of the suture may then be gripped and pulled to draw the first portion of the suture through the soft tissue so that a length of the first portion of the suture remains in the soft tissue between the point of insertion and exit point of the first end. The soft tissue may then be manually grouped and advanced along at least one portion of the suture to provide the desired amount of lift.

The medical devices of the present disclosure may be utilized in any cosmetic, orthopedic, open endoscopic or laparoscopic methods. In addition, sutures of the present disclosure may be utilized to attach one tissue to another including, but not limited to, attaching tissue to a ligament. Specific applications of cosmetic surgeries include, for example, facelifts, browlifts, thigh lifts, and breast lifts.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

We claim:

1. An apparatus for forming a barbed suture comprising:
a tool;
a converter operably connected to the tool for transmitting ultrasonic energy to the tool;
a gripper for supporting a suture relative to the tool; and
a motorized slide for moving the gripper in X, Y, and Z planes relative to the tool from a first position in which the gripper is laterally spaced from the tool to a second position in which the gripper is positioned adjacent the tool such that the suture contacts the tool.

2. The apparatus of claim 1, wherein the tool includes a horn.

3. The apparatus of claim 2, wherein the converter transmits ultrasonic energy to the horn.

4. The apparatus of claim 3, wherein the tool includes a blade secured to the horn.

5. The apparatus of claim 4, wherein the blade is one of a knife blade and a rotary blade.

6. The apparatus of claim 3, wherein a frequency of the ultrasonic energy transmitted to the horn is between about 1 kHz and about 100 kHz.

7. The apparatus of claim 3, wherein a signal amplitude of the ultrasonic energy transmitted to the horn is between about 1μ and 125μ.

8. The apparatus of claim 1, further including a camera and a light source for optimizing a view of the camera.

9. The apparatus of claim 1, further including a rotation motor for rotating a suture relative to the tool.

10. The apparatus of claim 1, wherein the gripper includes an anvil.

11. The apparatus of claim 1, further including an advance slide for moving a suture parallel to the tool.

12. The apparatus of claim 1, further including an ultrasonic generator for supplying ultrasonic energy to the convertor.

13. The apparatus of claim 12, wherein the converter converts electrical energy from the ultrasonic generator to mechanical energy.

* * * * *